(12) United States Patent
Ando et al.

(10) Patent No.: US 6,911,179 B2
(45) Date of Patent: Jun. 28, 2005

(54) OZONE DETECTING MATERIAL AND METHOD FOR DETECTING OZONE

(75) Inventors: Masanori Ando, Ikeda (JP); Otto S. Wolfbeis, Regensburg (DE); Vladimir M. Mirsky, Regensburg (DE)

(73) Assignee: National Institute of Advanced Industrial Science and Technology, Tokyo-to (JP)

( * ) Notice: Subject to any disclaimer, the term of this patent is extended or adjusted under 35 U.S.C. 154(b) by 241 days.

(21) Appl. No.: 10/189,171

(22) Filed: Jul. 5, 2002

(65) Prior Publication Data

US 2003/0148534 A1 Aug. 7, 2003

(30) Foreign Application Priority Data

Jul. 5, 2001 (JP) .......................................... 2001-204248

(51) Int. Cl.[7] .............................................. G01N 27/02
(52) U.S. Cl. .............................. 422/82.02; 422/82.01; 422/98
(58) Field of Search ........................... 436/85, 75, 106, 436/135; 422/82.02

(56) References Cited

U.S. PATENT DOCUMENTS

| | | | | |
|---|---|---|---|---|
| 3,963,498 A | * | 6/1976 | Trevoy ........................ | 430/631 |
| 4,803,138 A | * | 2/1989 | Kobayashi et al. .......... | 429/331 |
| 4,887,455 A | * | 12/1989 | Payne et al. ................ | 73/24.06 |
| 5,047,445 A | * | 9/1991 | Nishizawa ................... | 522/114 |
| 5,066,556 A | * | 11/1991 | Toyosawa et al. .......... | 429/213 |

FOREIGN PATENT DOCUMENTS

| | | | | |
|---|---|---|---|---|
| JP | 61214371 A | * | 9/1986 | .......... H01M/10/36 |
| JP | 63314760 A | * | 12/1988 | ............ H01M/4/02 |
| JP | 01069662 A | * | 3/1989 | .......... C08L/101/00 |

OTHER PUBLICATIONS

E. Jungreis, in: Spot Test Analysis, Wiley (1985) New York, ch. 6.2.30, p. 180.

Denys Amos, "Specific Spectrofluorometric Determination of Atmospheric Ozone Using 2–Diphenylacetyl–1, 3–Indandione–1–Hydrazone", Analytical Chemistry, vol. 42, No. 8, (Jul. 1970) pp 842–844.

* cited by examiner

*Primary Examiner*—Yelena G. Gakh
(74) *Attorney, Agent, or Firm*—Armstrong, Kratz, Quintos, Hanson & Brooks, LLP (57) ABSTRACT

The present invention provides an ozone detecting material comprising a polymer prepared by polymerization of at least one monomer selected from the group consisting of 2-, 3-, 4-halogen substituted anilines or aniline substituted with $C_{1-3}$-alkyl in N-position, and diphenylamine, formed into a thin film coated on a transparent substrate, waveguide, or optical fiber, or additionally comprising a component selected from electro-conductive fine carbon powder, a semiconductive metal oxide, or a semiconductive polymer material, and a method for detecting ozone comprising the steps of contacting this ozone detecting material with an ozone-containing gas and determining the light absorption rate and/or electrical conductivity of the ozone detecting material at that time.

3 Claims, 5 Drawing Sheets

OZONE DETECTING MATERIAL AND METHOD FOR DETECTING OZONE

BACKGROUND OF THE INVENTION (1) Field of the Invention

The present invention relates to an ozone detecting material for detecting a trace amount of ozone in a gas and a method for detecting ozone.

(2) Description of Related Art

Detecting the presence of a trace amount of ozone in a gas such as air and measuring the ozone concentration are important in view of industrial and environmental problems. In recent years, there has been a growing demand for the development of a material for detecting ozone in a gas such as air and an ozone detection method. This is because although ozone is highly useful as a clean oxidant not leaving any harmful residues when ozone breaks down and recently became more widely used as a bactericide and deodorant for water and air and as a cleaning agent in the semiconductor manufacturing industry, ozone before it breaks down is harmful, even in a trace amount, to the human body.

However, most conventional small-sized low concentration ozone generators used in hospitals, etc. are not equipped with ozone concentration monitors, etc. This is because conventional ozone detectors are large and expensive. Therefore, the development of a small-sized, economically producible ozone detector is desired. Desired is the development of an inexpensive high-sensitive ozone detecting material applicable to the production of such an ozone detector and a simple and easy ozone detection method enabling size reduction of a detector.

Known materials and methods for detecting a trace amount of ozone in a gas such as air include, for example, (1) a detection method utilizing ozone-specific light absorption in the ultraviolet wavelength region, (2) a detection method using the irreversible change in the visible light absorption of a colorant (e.g., indigo dyes) by a reaction with ozone, (3) a detection method using chemiluminescence, and (4) a detection method using the reversible change in the electrical conductivity of indium oxide or the like in a heated state caused by the presence of ozone.

However, these conventional methods have the following problems. In method (1), since very small absorbance changes caused by ozone must be detected, a gas cell with a long optical path length, an expensive high precision photodetector and a light source are required, resulting in a large expensive detector. In method (2), since colorant absorbance change due to ozone is irreversible, the method can be used for one-time only detection of ozone and cannot be used for continuous detection. In method (3), since each measurement requires the step of producing chemiluminescence, the method cannot be used for continuous ozone detection. In method (4), since an ozone detecting material such as indium oxide must be kept heated at a high temperature at all times, the procedure consumes a large amount of energy and a device comprising an ozone detecting material, electrodes, a heater, a voltage applicator, a voltmeter, an ammeter and a stabilization circuit is quite complicated and expensive.

Therefore, it is desired to develop an ozone detecting material and an ozone detection method for a simple-structured, economically producible, small-sized ozone detector. More specifically, desired are an ozone detecting material and an ozone detection method easily provided at low cost and enabling repeated measurement or continuous measurement, the material and method being capable of quickly detecting comparatively high-concentration ozone leakage from a small-sized ozone generator and pipelines by installing a large number of sensors on each ozone generator and each part of the pipelines, even when the ozone concentration is roughly indicated as a concentration region. Also desired are an ozone detecting material and an ozone detection method which can be used for one-time only measurement capable of retaining a record of the ozone detection for a certain period of time.

BRIEF SUMMARY OF THE INVENTION

An object of the present invention is to provide an ozone detecting material and an ozone detection method for a simple-structured, economically producible, small-sized ozone detector, the material and method enabling repeated measurement or continuous measurement. Another object is to provide an ozone detecting material and an ozone detection method enabling one-time only measurement which can retain a record of the ozone detection for a certain period of time.

The present invention was made to achieve the above objects. The present invention provides the following ozone detecting materials and ozone detection methods.

1. An ozone detecting material comprising a polymer prepared by polymerization of at least one monomer selected from the group consisting of aniline, aniline having a halogen substituent at the 2-position, aniline having a halogen substituent at the 3-position, aniline having a halogen substituent at the 4-position, aniline having a $C_{1-3}$ alkyl substituent at the N-position, toluidine and diphenylamine.

2. An ozone detecting material comprising a polymer prepared by polymerization of at least one monomer selected from the group consisting of aniline, 2-bromoaniline, 2-chloroaniline, 3-bromoaniline, 3-chloroaniline, 4-bromoaniline, 4-chloroaniline, N-methylaniline, N-ethylaniline, N-propylaniline, o-toluidine, m-toluidine, p-toluidine and diphenylamine.

3. The ozone detecting material according to item 1 which is formed into a thin film on a transparent substrate, a waveguide, an optical fiber or an electrode.

4. The ozone detecting material according to item 1which comprises the polymer of item 1 and at least one additive component selected from the group consisting of an electro-conductive fine carbon powder, a semiconductive metal oxide and a semiconductive polymer material, the ratio of the number of monomer units in the polymer of item 1 to the sum of the number of carbon atoms in the electro-conductive fine carbon powder, the number of atoms other than oxygen in the semiconductive metal oxide and the number of monomer units constituting the semiconductive polymer material being in the range of 1:0.01 to 1:1.

5. The ozone detecting material according to item 4 wherein the additive component is an electro-conductive fine carbon powder.

6. The ozone detecting material according to item 4wherein the semiconductive metal oxide is selected from the group consisting of tin oxide, indium oxide, titanium oxide, vanadium oxide, manganese oxide, iron oxide, nickel oxide, copper oxide and tungsten oxide.

7. The ozone detecting material according to item 4 wherein the semiconductive polymer material is selected from the group consisting of polypyrrole, polythiophene, poly(paraphenylene), poly(alkylpyrrole), poly(alkylthiophene), oligopyrrole and oligothiophene.

8. A method for detecting ozone comprising the steps of contacting the ozone detecting material of item 1 with an ozone-containing gas and determining the light absorption rate of the ozone detecting material at that time.

9. A method for detecting ozone comprising the steps of contacting the ozone detecting material of item 1 with an ozone-containing gas and determining the electrical conductivity of the ozone detecting material at that time.

The ozone detecting material of the invention can be simply and easily produced from low-cost materials and exhibits excellent long-term stability, chemical stability and mechanical strength in an ozone-free gas such as air.

The gas to be contacted with the ozone detecting material according to the ozone detection method of the invention is not specifically limited. Any gas in which ozone can be contained or present in various concentrations can be used. Specific examples include air, Ar, He, $CO_2$, and a mixture thereof. The humidity of these gases is not specifically limited and any gas in a dried state to a humid state can be used.

Examples of ozone detecting materials further include the following:

10. The ozone detecting material according to item 1 which comprises the polymer of item 1 and at least one additive component selected from the group consisting of a transparent oxide and a transparent polymer material, the ratio of the number of monomer units in the polymer of item 1 to the sum of the number of atoms other than oxygen in the oxide and the number of monomer units constituting the polymer material being in the range of 1:0.01 to 1:1.

11. The ozone detecting material according to item 10 wherein the transparent oxide is selected from the group consisting of $SiO_2$, $Al_2O_3$ and $ZrO_2$.

12. The ozone detecting material according to item 10 wherein the transparent polymer material is selected from the group consisting of an acrylic resin, a polycarbonate resin, a polystyrene resin and a polyvinyl resin.

13. The ozone detecting material according to item 1 wherein the polymer of item 1 is in the form of fine particles with a particle size of 1 $\mu$m or less and dispersed in at least one component selected from the group consisting of a transparent oxide and a transparent polymer material, the ratio of the number of monomer units in the polymer of item 1 to the sum of the number of atoms other than oxygen in the oxide and the number of monomer units constituting the polymer material being in the range of 1:1 to 1:100.

14. The ozone detecting material according to item 13 wherein the transparent oxide is selected from the group consisting of $SiO_2$, $Al_2O_3$ and $ZrO_2$.

15. The ozone detecting material according to item 13 wherein the transparent oxide is a porous glass comprising $SiO_2$ as a main component.

16. The ozone detecting material according to item 13 wherein the transparent polymer material is selected from the group consisting of an acrylic resin, a polycarbonate resin, a polystyrene resin and a polyvinyl resin.

17. The ozone detecting material according to item 1 wherein the polymer of item 1 is in the form of fine particles with a particle size of 1 $\mu$m or less and dispersed in at least one component selected from the group consisting of a semiconductive metal oxide and a semiconductive polymer material, the ratio of the number of monomer units in the polymer of item 1 to the sum of the number of atoms other than oxygen in the semiconductive metal oxide and the number of monomer units constituting the semiconductive polymer material being in the range of 1:1 to 1:100.

DETAILED DESCRIPTION OF THE INVENTION

The monomer of the "polymer" used as an ozone detecting material of the invention is aniline and its derivatives. Examples of such monomers include aniline, aniline having a halogen substituent at the 2-position, aniline having a halogen substituent at the 3-position, aniline having a halogen substituent at the 4-position, aniline having a $C_{1-3}$ alkyl substituent at the N-position, toluidine and diphenylamine. Specific examples include aniline, 2-bromoaniline, 2-chloroaniline, 3-bromoaniline, 3-chloroaniline, 4-bromoaniline, 4-chloroaniline, N-methylaniline, N-ethylaniline, N-propylaniline, o-toluidine, m-toluidine, p-toluidine and diphenylamine. These monomers can be used singly or in combinations of two or more.

The reduction-oxidation state (redox state) and the protonation degree of the "polymer" used as an ozone detecting material of the invention are not specifically limited. The reduction-oxidation state of the polymer can be, for example, a reduced state, an intermediate reduction-oxidation state or an oxidized state. The protonation degree of the polymer can be, for example, a protonated state, a partially protonated state or a deprotonated state. Polymers in any combination of such reduction-oxidation states and such protonation degrees can be used. Preferred examples of polymers include polyaniline, poly(2-chloroaniline) and poly(N-methylaniline), each of which can be in various reduction-oxidation states and various protonation degrees. Not only the above-mentioned homopolymers but also copolymers of two or more monomers can be used. Useful polymers further include mixtures of two or more homopolymers or copolymers of two or more different monomers.

The average polymerization degree of the polymer is not specifically limited but preferably in the range of 10 to 20000, more preferably 20 to 20000.

In the invention, the ozone detecting material is not specifically limited in shape but can be formed into various desired shapes such as thin films, powders or pellets in accordance with the ozone detection method. In optical ozone detection, for example, when the light absorption rate is measured by the transmission method described later, the ozone detecting material is usually formed into a thin film. When the light absorption rate is measured by the diffuse reflection method, the ozone detecting material is usually formed into a powder or pellets formed from the powder. In electrical ozone detection, the detecting material is formed into various desired shapes such as thin films or pellets, in accordance with the configuration of electrodes such as flat plates, interdigital shapes or wires.

When used as the ozone detecting material of the invention in the form of a thin film, the polymer is formed on a transparent substrate, on a waveguide, on the surface of an optical fiber or on an electrode in the form of a flat plate, interdigital shape, wire or the like.

The polymer used in the invention can be complexed with a component which is not capable of detecting ozone but has the function of facilitating the production of the polymer thin film or the like, improving the ozone detection capability of the polymer or enhancing the structural stability and mechanical strength of the polymer thin film. When used as an electrical ozone detection material, the polymer can be complexed with an optically transparent component or an optically opaque component. When used as an optical ozone detection material, the polymer can be complexed with a highly optically transparent component. Such complexation can be made by either of the following methods: adding a complex component to the polymer; adding the polymer to a complex component; dispersing the polymer into a complex component such as a porous material; and coating the polymer thin film or pellets with a complex component.

The mechanism of improving the ozone detection capability of the polymer by complexing the polymer with other components will be described below in detail. Generally, when the polymer is in a reduced and deprotonated state, it has a low electrical conductivity similar to that of an insulator. Therefore, when such a polymer is used as an electrical ozone detection material, the electric resistance tends to be too high and causes difficulty in measurement. By adding a component having slightly high electrical conductivity such as an electro-conductive fine carbon powder, an electro-conductive (semiconductive) metal oxide or an electro-conductive (semiconductive) polymer material, the basic electric resistance of the complex in an ozone-free gas is reduced to a value suitable for measurement, thus enhancing the usefulness of the polymer as an electrical ozone detection material. In addition, such complexation can improve the mechanical strength of the polymer. By selecting the acidity or basicity and reduction-oxidation state of the additive component, the polymer complex is provided with enhanced long-term stability. Examples of such semiconductive metal oxides include tin oxide, indium oxide, titanium oxide, vanadium oxide, manganese oxide, iron oxide, nickel oxide, copper oxide and tungsten oxide. Examples of semiconductive polymer materials include polypyrrole, polythiophene, poly(paraphenylene), poly(alkylpyrrole), poly(alkylthiophene), oligopyrrole and oligothiophene. The ratio of the number of monomer units in the polymer to the sum of the number of carbon atoms in the electro-conductive fine carbon powder, the number of atoms other than oxygen in the semiconductive metal oxide and the number of monomer units constituting the semiconductive polymer material is preferably in the range of about 1:0.01 to about 1:1.

The polymer can be pulverized into fine particles with a particle size of 1 $\mu$m or less and dispersed into a component such as a semiconductive metal oxide or a semiconductive polymer material. In this case, the ratio of the number of monomer units in the polymer to the sum of the number of atoms other than oxygen in the semiconductive metal oxide and the number of monomer units constituting the semiconductive polymer material is preferably in the range of about 1:1 to about 1:100.

As compared with the polymer alone, a complex of the polymer with a transparent polymer material such as polyvinyl alcohol or acrylic resin (e.g., poly(methylmethacrylate)) or a transparent glass has enhanced mechanical strength. In addition, such complexation can reduce light scattering and loss of incident light, thus enhancing the usefulness of the polymer as an optical ozone detection material. As compared with using the polymer alone as an ozone detecting material, the polymer complex (dispersion) formed by attaching the polymer to the inner wall of fine pores of a porous transparent material such as a porous glass or a porous transparent resin has a larger specific surface area and thus can more readily contact with any ozone added to a gas, thereby causing quicker and larger electrical and optical changes of the polymer by ozone. In this case, the polymer is preferably in the form of fine particles with a particle size of 1 $\mu$m or less. The transparent component to be complexed with the polymer is not specifically limited. Examples of transparent components include glass or quartz comprising $SiO_2$ as a main component; sapphire comprising $Al_2O_3$; $ZrO_2$ and like transparent oxides; acrylic resins, polycarbonate resins, polystyrene resins, polyvinyl resins and like transparent polymer materials.

The ratio of the number of monomer units in the polymer to the sum of the number of atoms other than oxygen in the transparent oxide of the complex component and the number of monomer units constituting the transparent polymer material of the complex component is preferably in the range of about 1:0.01 to about 1:100. When a complex component is added, the ratio of the number of monomer units in the polymer to the sum of the number of atoms other than oxygen in the transparent oxide of the complex component and the number of monomer units constituting the transparent polymer material of the complex component is preferably in the range of about 1:0.01 to about 1:1. When the polymer is formed into fine particles with a particle size of 1 $\mu$m or less and dispersed into a complex component, the ratio of the number of monomer units in the polymer to the sum of the number of atoms other than oxygen in the transparent oxide of the complex component and the number of monomer units constituting the transparent polymer material of the complex component is preferably in the range of about 1:1 to about 1:100.

The ozone detection selectivity of the polymer can be improved by coating a thin film or pellets of the polymer with a layer of a component capable of blocking or adsorbing gases other than ozone which may impede ozone detection.

The light absorption rate and/or electrical conductivity of the ozone detecting material of the invention varies in accordance with changes in the ozone concentration of the contact gas. Using this property, ozone can be optically detected in the following manner. In the ozone detection method of the invention, the light absorption rate of the ozone detecting material upon contact with an ozone-containing gas is measured. The light absorption rate of the ozone detecting material can be measured by known methods. Useful methods include, for example, various known methods such as a method of determining the light absorption rate from the light intensity transmitted through a transparent substrate and a thin ozone detecting material layer formed thereon; a method of estimating the light absorption rate by irradiating an ozone detecting material in the form of a powder or pellets formed by compressing the powder and measuring the reflected light intensity by the diffuse reflection method; a method of measuring the light absorption rate of an ozone detecting material attached to the surface of an optical waveguide or an optical fiber; and a method of measuring the light absorption rate by using the photoacoustic effect. Using such a known method and the ozone detecting material of the invention, ozone in a gas can be detected or measured by measuring the optical absorption rate. The wavelength of light used for measuring the light absorption rate is not specifically limited but is preferably in the range of about 250 to about 2,500 nm.

Examples of transparent substrates on which the thin film as an optical ozone detection material is formed are those made of the following materials: glass or quartz comprising $SiO_2$ as a main component; sapphire comprising $Al_2O_3$; ZnO, $ZrO_2$ or like transparent oxides; acrylic resins, polycarbonate resins, polystyrene resins, polyvinyl resins or like transparent polymer materials; or ZnSe or the like. These materials are usually used in the form of flat plates. Thin films of these materials can be formed on the surface of a waveguide and used. When a thin detecting material film is formed on a waveguide, the light passing through the waveguide is multiply reflected at the interface between the waveguide and the thin film and evanescent waves pass into the thin film, thus increasing optical ozone detection sensitivity. Instead of using a waveguide, the optical ozone detection sensitivity can also be increased by forming a thin ozone detecting material film on the surface of an optical fiber whose clad portion has been thinned or removed. The thickness of the thin film is not specifically limited. When the thin film is too thin, sufficient sensitivity (absorbance changes by ozone) is not obtained. When the film is too thick, excessive light absorption and too little transmitted light result, which makes the detection of absorbance change difficult. Therefore, the thickness of the thin film is preferably in the range of about 100 nm to about 10 $\mu$m.

When used as an electrical ozone detection material, the polymer in the form of a thin film or pellets (the form is not specifically limited) can be formed on a metal electrode such as gold, platinum, copper or aluminium, or on a transparent oxide electrode such as tin oxide, indium oxide or ITO. The shape of the electrode is not specifically limited. For example, flat plate-shaped or interdigital electrodes can be used. The thickness of the thin film is not specifically limited. When the thin film is too thin, sufficient sensitivity (electric resistance change by ozone) is not obtained. When the film is too thick, there is an excessively large electric resistance and/or a larger portion of the film is unrelated to the current pathway which is wasteful. Therefore, the thickness of the thin film is preferably in the range of about 100 nm to about 10 $\mu$m. The electrical conductivity of the ozone detecting material can be measured by known methods such as the direct current method, the alternating current method and the like.

In the present invention, used as the main component of the ozone detecting material is a polymer obtained by polymerization of at least one monomer selected from the group consisting of aniline, aniline having a halogen substituent at the 2-position, aniline having a halogen substituent at the 3-position, aniline having a halogen substituent at the 4-position, aniline having a $C_{1-3}$ alkyl substituent at the N-position, toluidine and diphenylamine. These polymers have the property that their light absorption rate or electrical conductivity changes in the presence of ozone and are used as optical ozone detection materials or electrical ozone detection materials. The reason why the polymers have such a property has not yet been established but it is believed to be based on the following principle.

These polymers have a continuous absorption band in a wide wavelength range of ultraviolet—visible—near infrared ray. Such a broad absorption spectrum is based on the semiconductive electronic structure of the polymer. The electronic structure and light absorption characteristics of these polymers can be represented by those of polyaniline. Polyaniline can exist in various states which reversibly change between one another in accordance with the reduction-oxidation state and the degree of protonation; and polyaniline in each state shows unique light absorption characteristics and electrical conductivity. Typical states of polyaniline are an ashy brown low electro-conductive leucoemeraldine base, a blue low electro-conductive emeraldine base, a purple low electro-conductive pernigraniline base, and a green high electro-conductive emeraldine salt. When polyaniline in one of such mutually reversible states is retained in a gas and ozone is added to the gas, the ozone gas with its strong oxidative power oxidizes polyaniline in a reduced state into an oxidized state. Presumably, ozone reacts with a proton of polyaniline in a protonated state, thus changing the protonation degree of polyaniline. To what extent the oxidation and/or protonation degree of polyaniline is changed by ozone is dependent on the concentration of ozone. Therefore, it is presumed that the oxidation and/or the protonation degree of polyaniline changes in accordance with the ozone concentration, which causes polyaniline absorbance change and electrical conductivity change by ozone. When polyaniline is contacted with an ozone-containing gas and then retained in an ozone-free gas, the absorbance and electrical conductivity of polyaniline tends to hardly recover, partially recover or almost completely recover to their original states depending on the original state of polyaniline (before contact with ozone). By using such differences in reversibility/irreversibility and recovery rate, one can selectively prepare an ozone detecting material for one-time only measurement suitable for recording ozone leakage or an ozone detecting material capable of repeated or continuous detection. To what extent the absorbance and electrical conductivity are changed by ozone and to what degree these changes are dependent on the ozone concentration vary in accordance with the original state of polyaniline (before contact with ozone). For example, it is possible to selectively prepare a material whose absorbance and electrical conductivity greatly change in the presence of a low concentration of ozone and are saturated in the high concentration region, and a material whose absorbance and electrical conductivity slightly change in the presence of a low concentration of ozone and are not saturated even in the high concentration region.

Not all polymers, i.e., not all polymer materials exhibit such phenomena. Only polymers (high polymers) satisfying the following three conditions are deemed to achieve the phenomena:

(1) the polymer has a broad light absorption band ranging from ultraviolet, through visible, to near infrared wavelengths and a certain level of electrical conductivity (near the semiconductor range);
(2) reduction-oxidation is possible; and
(3) protonation and/or deprotonation is possible.

All the above-mentioned polymers obtained by polymerization of at least one monomer selected from the group consisting of aniline, aniline having a halogen substituent at the 2-position, aniline having a halogen substituent at the 3-position, aniline having a halogen substituent at the 4-position, aniline having a $C_{1-3}$ alkyl substituent at the N-position, toluidine and diphenylamine satisfy these three conditions and have excellent optical ozone detection capability and/or excellent electrical ozone detection capability.

When the polymer is formed into a thin film and used as an optical ozone detection material, the thin film is usually formed on a transparent substrate such as glass, quartz, sapphire, an acrylic resin, a polycarbonate resin, a polystyrene resin or a polyvinyl resin, or on the surface of a waveguide or an optical fiber. In the case of using an optical fiber, the clad portion is usually thinned or partially or entirely removed. When the polymer is formed into a thin film and used as an electrical ozone detection material, the thin film is usually formed on a metal electrode such as gold, platinum, copper or aluminium, or on a transparent electrode such as tin oxide, indium oxide or ITO. The shape of the electrode is not specifically limited. Electrodes in the form of flat plates, interdigital shapes, wires or the like can be used. The method of forming a thin film is not specifically limited but various known methods can be used. Useful methods include, for example, chemical polymerization methods such as the chemical oxidation polymerization method, and electrochemical polymerization methods such as the electrolytic oxidation polymerization method. When the polymer is soluble, the polymer solution can be applied to a substrate by the dip coating method, the spin coating method, the spraying method, the screen printing method or the like, or the polymer powder can be dispersed in a solvent and applied to a substrate by the dip coating method, the spin coating method, the spraying method, the screen printing method or the like and dried. In order to control the range of ozone concentration to which the polymer makes an optical and/or electric response and the reversibility or irreversibility thereof, the polymer is treated with an oxidant or a reducing agent to control the reduction-oxidation state or treated with an acidic or basic solution to control the protonated or deprotonated state.

When used as an optical ozone detection material, the thin film is not specifically limited in thickness. However, when the thin film is too thin, sufficient sensitivity (absorbance change by ozone) is not obtained. When the film is too thick, excessive light absorption and too little transmitted light result, making the detection of absorbance change difficult. The thickness of the thin film is preferably in the range of about 100 nm to about 10 $\mu$m.

When used as an electrical ozone detection material, the thin film is not specifically limited in thickness. When the thin film is too thin, sufficient sensitivity (electric resistance change by ozone) is not obtained. When the film is too thick, there is an excessively large electric resistance and/or a larger portion of the film is unrelated to the current pathway which is wasteful. Therefore, the thickness of the thin film is preferably in the range of about 100 nm to about 10 $\mu$m. When used as an electrical ozone detection material, the polymer can be used in the form of pellets. For example, the polymer can be formed into pellets directly on the surface of an electrode, or the polymer in the form of a powder or a thick solution or a mixture of the polymer and a solvent can be formed with an electrode embedded therein.

The present invention provides an ozone detecting material using a low-cost material such as aniline, which exhibits high optical sensitivity (absorbance change) and/or high electric sensitivity (electrical conductivity change) in response to a trace amount of ozone in a gas such as air. The present invention provides an ozone detection method by absorbance change measurement and/or electrical conductivity measurement using a simple material.

It is possible to control the ozone concentration range in which the ozone detecting material of the invention can exhibit high optical sensitivity and/or high electric sensitivity and reversibility or irreversibility of the optical sensitivity and/or electric sensitivity by suitably selecting the raw material, production method and treatment method.

The ozone detecting material of the invention has excellent long-term stability, chemical stability and mechanical strength and can easily be produced at low cost.

The ozone detection method of the invention can be used for repeated measurement or continuous measurement or for one-time only measurement capable of retaining a record of the ozone detection for a certain period of time.

EXAMPLES

The following Examples are provided to illustrate the invention in more detail and are not to limit the scope of the invention.

Example 1

A polyaniline thin film was formed on a polystyrene substrate (the inner walls of a polystyrene cuvette) by chemical oxidation polymerization and washed with distilled water and dried, thus giving a blue polyaniline thin film (about 500 nm in thickness) in an intermediate reduction-oxidation and intermediate protonation state. Two polyaniline thin films, with a total thickness of about 1000 nm, were exposed to air with a relative humidity of 50% and then subjected to air to which 2.5 ppm, 10 ppm, 25 ppm, 50 ppm or 100 ppm of ozone was added. The visible to near-IR absorbance of the polyaniline thin film did not change in the presence of 25 ppm or less of ozone but changed in the presence of 50 ppm or 100 ppm of ozone. Under exposure to 100 ppm of ozone, the change in absorbance of the polyaniline thin film was maximal (largest increase) at a wavelength of around 700 nm. Under exposure to 50 ppm and 100 ppm of ozone, the absorbance change ratio of the polyaniline thin film was maximal (largest increase) (0.100 and 0.293, respectively) at a wavelength of around 650 nm.

Figure 1:
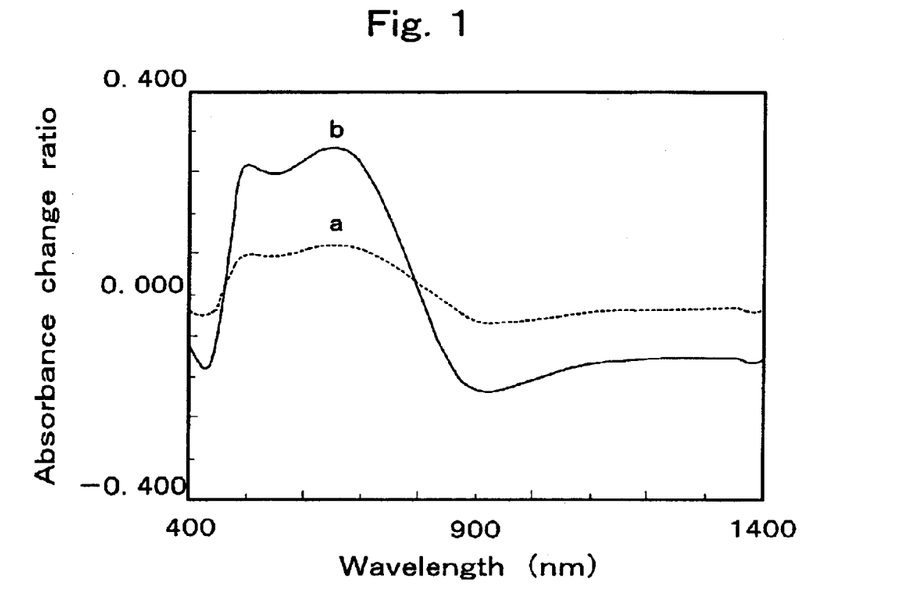
FIG. 1 shows the relationship between the absorbance change ratio of a polyaniline thin film and the wavelength of light in Example 1.

Absorbance change ratio=(absorbance in the ozone-containing air–absorbance in the ozone-free air)/absorbance in the ozone-free air FIG. 1 shows the relationship between the absorbance change ratio of the polyaniline thin film and the wavelength of light. In FIG. 1, the ozone concentrations are 50 ppm (a) and 100 ppm (b). When the atmosphere was changed from the ozone-containing air to an ozone-free air, the absorbance of the polyaniline thin film gradually returned to the original absorbance of the film before addition of ozone to the air. The results show that this polyaniline thin film is useful as an optical sensing material for detection of a relatively high concentration of ozone. When ozone was added to air with a relative humidity of 20% and to air with a relative humidity of 80%, results similar to the above were obtained. When the polyaniline thin film was formed on a glass substrate and on a quartz substrate by chemical oxidation polymerization, absorbance changes due to ozone were similar to the above.

Example 2

A polyaniline thin film was formed on a polystyrene substrate (the inner walls of a polystyrene cuvette) by chemical oxidation polymerization. The resulting film was reduced with a reducing agent, washed with an aqueous sodium hydroxide solution and dried, thus giving a purple polyaniline thin film (about 500 nm in thickness) in a reduced and deprotonated state. Two polyaniline thin films, with a total thickness of about 1000 nm, were exposed to air with a relative humidity of 50% and then subjected to air to which 2.5 ppm, 10 ppm, 25 ppm, 50 ppm or 100 ppm of ozone was added. The visible to near-IR absorbance of the polyaniline thin film did not change in the presence of 10 ppm or less of ozone but changed in the presence of 25 ppm, 50 ppm or 100 ppm of ozone. Under exposure to 100 ppm of ozone, the change in absorbance of the polyaniline thin film was maximal (largest increase) at a wavelength of around 500 nm. Under exposure to 50 ppm and 100 ppm of ozone, the absorbance change ratio of the polyaniline thin film was maximal (largest increase) (0.092 and 0.154, respectively) at a wavelength of around 490 nm. When the atmosphere was changed from the ozone-containing air to an ozone-free air, the absorbance of the polyaniline thin film gradually returned to the original absorbance of the film before addition of ozone to the air. The results show that this polyaniline thin film is useful as an optical sensing material for detection of a relatively high concentration of ozone.

Example 3

A polyaniline thin film was formed on a polystyrene substrate (the inner walls of a polystyrene cuvette) by chemical oxidation polymerization. The resulting film was reduced with a reducing agent, washed with distilled water and dried, thus giving a green polyaniline thin film (about 500 nm in thickness) in a reduced and intermediate protonation state. Two polyaniline thin films, with a total thickness of about 1000 nm, were exposed to air with a relative humidity of 50% and then subjected to air to which 2.5 ppm, 10 ppm, 25 ppm, 50 ppm or 100 ppm of ozone was added. The visible to near-IR absorbance of the polyaniline thin film did not change in the presence of 10 ppm or less of ozone but changed in the presence of 25 ppm, 50 ppm or 100 ppm of ozone. Under exposure to 100 ppm of ozone, the change in absorbance of the polyaniline thin film was maximal (largest increase) at a wavelength of around 750 nm. Under exposure to 50 ppm and 100 ppm of ozone, the absorbance change ratio of the polyaniline thin film was maximal (largest increase) (0.287 and 0.674, respectively) at a wavelength of around 620 nm. When the atmosphere was changed from the ozone-containing air to an ozone-free air, the absorbance of the polyaniline thin film gradually returned to the original absorbance of the film before addition of ozone to the air. The results show that this polyaniline thin film is useful as an optical sensing material for detection of a relatively high concentration of ozone. When ozone was added to air with a relative humidity of 20% and to air with a relative humidity of 80%, results similar to the above were obtained. Electrodes were attached to a polyaniline thin film formed on a glass substrate by chemical oxidation polymerization as above and to polyaniline pellets formed by compressing the powder. The electrical conductivity change of the polyaniline thin film when exposed to 100 ppm of ozone was measured. The results show that electrical conductivity of the polyaniline thin film increases in the presence of ozone and the thin film is useful as an electrical sensing material for ozone detection.

Example 4

Figure 2:
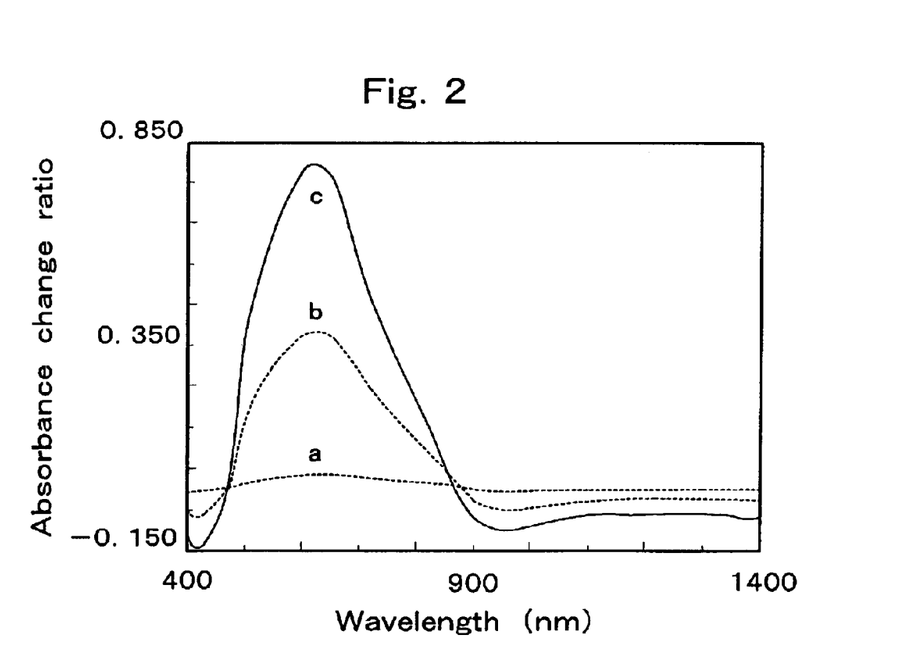
FIG. 2 shows the relationship between the absorbance change ratio of a polyaniline thin film and the wavelength of light in Example 4.

A polyaniline thin film was formed on a polystyrene substrate (the inner walls of a polystyrene cuvette) by chemical oxidation polymerization. The resulting film was reduced with a reducing agent, washed with hydrochloric acid and dried, thus giving a green polyaniline thin film (about 500 nm in thickness) in a reduced and protonated state. Two polyaniline thin films, with a total thickness of about 1000 nm, were exposed to air with a relative humidity of 50% and then subjected to air to which 2.5 ppm, 10 ppm, 25 ppm, 50 ppm or 100 ppm of ozone was added. The visible to near-IR absorbance of the polyaniline thin film did not change in the presence of 10 ppm or less of ozone but changed in the presence of 25 ppm, 50 ppm or 100 ppm of ozone. Under exposure to 100 ppm of ozone, the change in absorbance of the polyaniline thin film was maximal (largest increase) at a wavelength of around 750 nm. Under exposure to 25 ppm, 50 ppm and 100 ppm of ozone, the absorbance change ratio of the polyaniline thin film was maximal (largest increase) (0.041, 0.383 and 0.801, respectively) at a wavelength of around 620 nm. FIG. 2 shows the relationship between the absorbance change ratio of the polyaniline thin film and the wavelength of light. In FIG. 2, the ozone concentrations are 25 ppm (a), 50 ppm (b) and 100 ppm (c). When the atmosphere was changed from the ozone-containing air to an ozone-free air, the absorbance of the polyaniline thin film gradually returned to the original absorbance of the film before addition of ozone to the air. The results show that this polyaniline thin film is useful as an optical sensing material for detection of intermediate to high concentrations of ozone. When ozone was added to air with a relative humidity of 20% and to air with a relative humidity of 80%, results similar to the above were obtained.

Example 5

Figure 3:
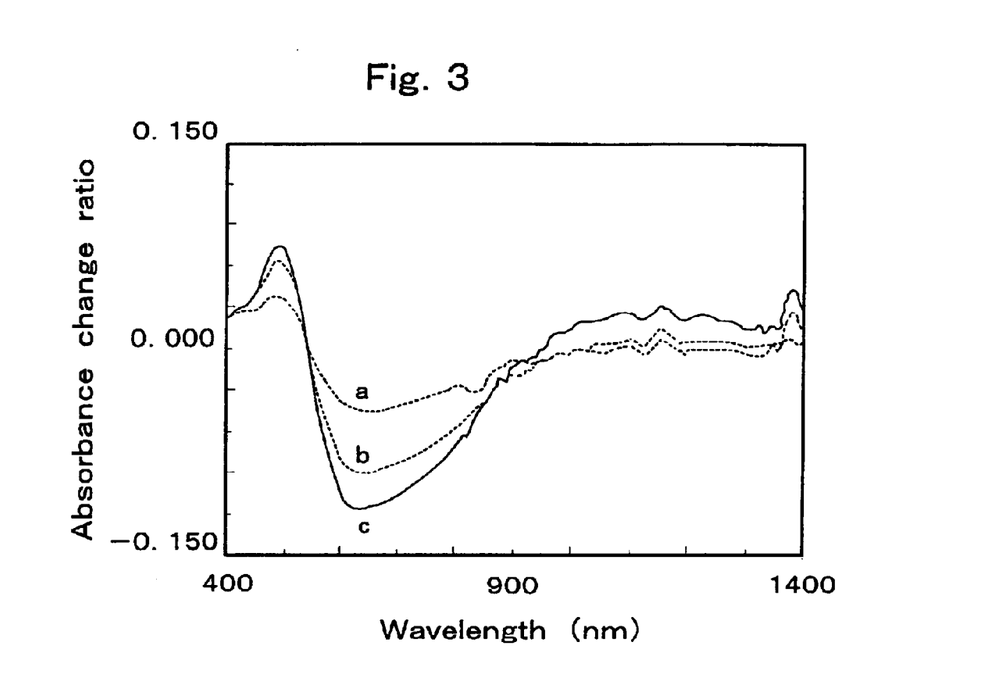
FIG. 3 shows the relationship between the absorbance change ratio of a polyaniline thin film and the wavelength of light in Example 5.

A polyaniline thin film was formed on a polystyrene substrate (the inner walls of a polystyrene cuvette) by chemical oxidation polymerization. The resulting film was oxidized with an oxidant, washed with an aqueous sodium hydroxide solution and dried, thus giving a purple polyaniline thin film (about 500 nm in thickness) in an oxidized and deprotonated state. Two polyaniline thin films, with a total thickness of about 1000 nm, were exposed to air with a relative humidity of 50% and then subjected to air to which 2.5 ppm, 10 ppm, 25 ppm, 50 ppm or 100 ppm of ozone was added. The visible to near-IR absorbance of the polyaniline thin film did not change in the presence of 10 ppm or less of ozone but changed in the presence of 25 ppm, 50 ppm or 100 ppm of ozone. Under exposure to 100 ppm of ozone, change in absorbance of the polyaniline thin film was maximal (largest-decrease) at a wavelength of around 610 nm. Under exposure to 25 ppm, 50 ppm and 100 ppm of ozone, the absorbance change ratio of the polyaniline thin film was maximal (largest decrease) (−0.047, −0.091 and −0.117, respectively) at a wavelength of around 640 nm. FIG. 3 shows the relationship between the absorbance change ratio of the polyaniline thin film and the wavelength of light. In FIG. 3, the ozone concentrations are 25 ppm (a), 50 ppm (b) and 100 ppm (c). When the atmosphere was changed from the ozone-containing air to an ozone-free air, the absorbance of the polyaniline thin film gradually returned to the original absorbance of the film before addition of ozone to the air. The results show that this polyaniline thin film is useful as an optical sensing material for detection of intermediate to high concentrations of ozone.

Example 6

Figure 4:
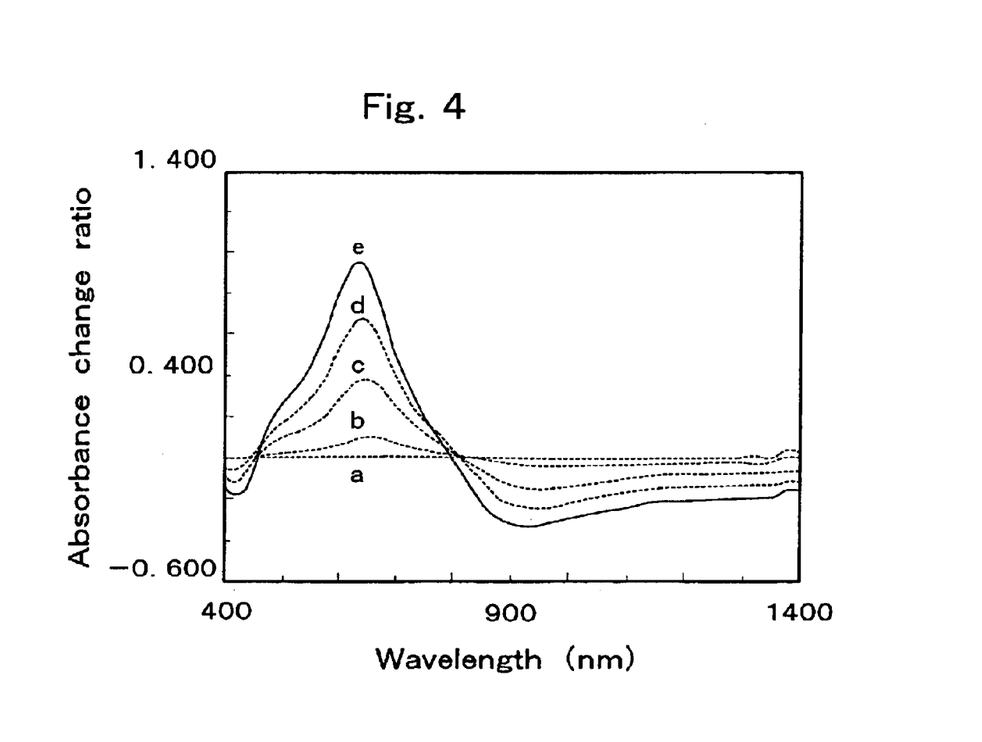
FIG. 4 shows the relationship between the absorbance change ratio of a polyaniline thin film and the wavelength of light in Example 6.

A polyaniline thin film was formed on a polystyrene substrate (the inner walls of a polystyrene cuvette) by chemical oxidation polymerization. The resulting film was oxidized with an oxidant, washed with hydrochloric acid and dried, thus giving a green polyaniline thin film (about 500 nm in thickness) in an oxidized and protonated state. Two polyaniline thin films, with a total thickness of about 1000 nm, were exposed to air with a relative humidity of 50% and then subjected to air to which 2.5 ppm, 10 ppm, 25 ppm, 50 ppm or 100 ppm of ozone was added. The visible to near-IR absorbance of the polyaniline thin film changed in the presence of ozone in all of the above concentrations. Under exposure to 100 ppm of ozone, the change in absorbance of the polyaniline thin film was maximal (largest increase) at a wavelength of around 690 nm. Under exposure to 2.5 ppm, 10 ppm, 25 ppm, 50 ppm and 100 ppm of ozone, the absorbance change ratio of the polyaniline thin film was maximal (largest increase) (0.012, 0.102, 0.388, 0.685 and 0.965, respectively) at a wavelength of around 650 nm. FIG. 4 shows the relationship between the absorbance change ratio of the polyaniline thin film and the wavelength of light. In FIG. 4, the ozone concentrations are 2.5 ppm (a), 10 ppm (b), 25 ppm (c), 50 ppm (d) and 100 ppm (e). When the atmosphere was changed from the ozone-containing air to an ozone-free air, the absorbance of the polyaniline thin film gradually returned to the original absorbance of the film before addition of ozone to the air. The results show that this polyaniline thin film is useful as an optical sensing material for the detection of ozone over a wide range of concentrations. When ozone was added to air with a relative humidity of 20% and to air with a relative humidity of 80%, results similar to the above were obtained.

Example 7

A poly(N-methylaniline) thin film was formed on a polystyrene substrate (the inner walls of a polystyrene cuvette) by chemical oxidation polymerization. The resulting film was washed with distilled water and dried, thus giving a green poly(N-methylaniline) thin film (about 600 nm in thickness) in an intermediate reduction-oxidation and intermediate protonation state. Two poly(N-methylaniline) thin films, with a total thickness of about 1200 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(N-methylaniline) thin film did not change in the presence of 25 ppm or less of ozone but changed in the presence of 50 ppm or 100 ppm of ozone. Under exposure to 100 ppm of ozone, the change in absorbance of the poly(N-methylaniline) thin film was maximal (largest increase) at a wavelength of around 850 nm. Under exposure to 50 ppm and 100 ppm of ozone, the absorbance change ratio of the poly(N-methylaniline) thin film was maximal (largest increase) (0.010 and 0.112, respectively) at a wavelength of around 850 nm. When the atmosphere was changed from the ozone-containing air to an ozone-free air, the absorbance of the poly(N-methylaniline) thin film gradually returned to the original absorbance of the film before addition of ozone to the air. The results show that this poly(N-methylaniline) thin film is useful as an optical sensing material for detection of a relatively high concentration of ozone. When ozone was added to air with a relative humidity of 20% and to air with a relative humidity of 80%, results similar to the above were obtained. When the poly(N-methylaniline) thin film was formed on a glass substrate and on a quartz substrate by chemical oxidation polymerization, absorbance changes due to ozone were similar to the above.

Example 8

A poly(N-methylaniline) thin film was formed on a polystyrene substrate (the inner walls of a polystyrene cuvette) by chemical oxidation polymerization. The resulting films were reduced with a reducing agent, washed with distilled water and dried, thus giving a green poly(N-methylaniline) thin film (about 600 nm in thickness) in a reduced and intermediate protonation state. Two poly(N-methylaniline) thin films, with a total thickness of about 1200 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(N-methylaniline) thin film did not change in the presence of 25 ppm or less of ozone but changed in the presence of 50 ppm or 100 ppm of ozone. Under exposure to 100 ppm of ozone, the change in absorbance of the poly(N-methylaniline) thin film was maximal (largest increase) at a wavelength of around 820 nm. Under exposure to 50 ppm and 100 ppm of ozone, the absorbance change ratio of the poly(N-methylaniline) thin film was maximal (largest increase) (0.068 and 0.137, respectively) at a wavelength of around 780 nm. When the atmosphere was changed from the ozone-containing air to an ozone-free air, the absorbance of the poly(N-methylaniline) thin film gradually returned to the original absorbance of the film before addition of ozone to the air. The results show that this poly(N-methylaniline) thin film is useful as an optical sensing material for detection of a relatively high concentration of ozone. When ozone was added to air with a relative humidity of 20% and to air with a relative humidity of 80%, results similar to the above were obtained.

Example 9

Figure 5:
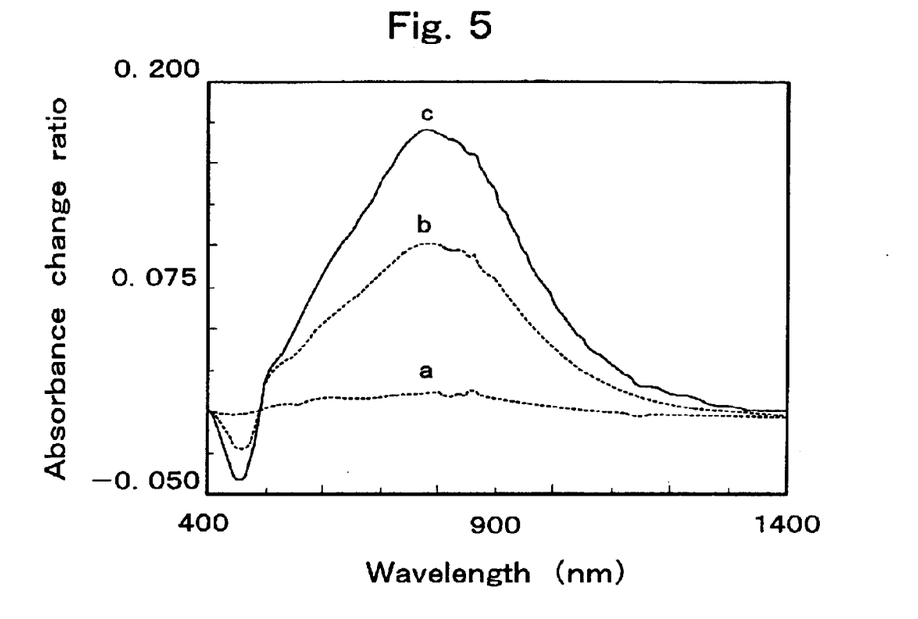
FIG. 5 shows the relationship between the absorbance change ratio of a poly(N-methylaniline) thin film and the wavelength of light in Example 9.

A poly(N-methylaniline) thin film was formed on a polystyrene substrate (the inner walls of a polystyrene cuvette) by chemical oxidation polymerization. The resulting film was reduced with a reducing agent, washed with hydrochloric acid and dried, thus giving a green poly(N-methylaniline) thin film (about 600 nm in thickness) in a reduced and protonated state. Two poly(N-methylaniline) thin films, with a total thickness of about 1200 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(N-methylaniline) thin film did not change in the presence of 10 ppm or less of ozone but changed in the presence of 25 ppm, 50 ppm or 100 ppm of ozone. Under exposure to 100 ppm of ozone, the change in absorbance of the poly(N-methylaniline) thin film was maximal (largest increase) at a wavelength of around 850 nm. Under exposure to 25 ppm, 50 ppm and 100 ppm of ozone, the absorbance change ratio of the poly(N-methylaniline) thin film was maximal (largest increase) (0.015, 0.104 and 0.174, respectively) at a wavelength of around 770 nm. FIG. 5 shows the relationship between the absorbance change ratio of the poly(N-methylaniline) thin film and the wavelength of light. In FIG. 5, the ozone concentrations are 25 ppm (a), 50 ppm (b) and 100 ppm (c). When the atmosphere was changed from the ozone-containing air to an ozone-free air, the absorbance of the poly(N-methylaniline) thin film gradually returned to the original absorbance of the film before addition of ozone to the air. The results show that this poly(N-methylaniline) thin film is useful as an optical sensing material for detection of a relatively high concentration of ozone. When ozone was added to air with a relative humidity of 20% and to air with a relative humidity of 80%, results similar to the above were obtained. Electrodes were attached to a poly(N-methylaniline) thin film formed on a glass substrate by chemical oxidation polymerization as above and to poly(N-methylaniline) pellets formed by compressing the powder.

The electrical conductivity change of the poly(N-methylaniline) thin film when exposed to 100 ppm of ozone was measured. The results show that electrical conductivity of the poly(N-methylaniline) thin film increases in the presence of ozone and the thin film is useful as an electrical sensing material for ozone detection.

Example 10

A poly(N-methylaniline) thin film was formed on a polystyrene substrate (the inner walls of a polystyrene cuvette) by chemical oxidation polymerization. The resulting film was oxidized with an oxidant, washed with an aqueous sodium hydroxide solution and dried, thus giving an ashy purple poly(N-methylaniline) thin film (about 600 nm in thickness) in an oxidized and deprotonated state. Two poly(N-methylaniline) thin films, with a total thickness of about 1200 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(N-methylaniline) thin film did not change in the presence of 10 ppm or less of ozone but changed in the presence of 25 ppm, 50 ppm or 100 ppm of ozone. Under exposure to 100 ppm of ozone, the change in absorbance of the poly(N-methylaniline) thin film was maximal (largest increase) at a wavelength of around 850 nm. Under exposure to 25 ppm, 50 ppm and 100 ppm of ozone, the absorbance change ratio of the poly(N-methylaniline) thin film was maximal (largest increase) (0.035, 0.054 and 0.077, respectively) at a wavelength of around 850 nm. When the atmosphere was changed from the ozone-containing air to an ozone-free air, the absorbance of the poly(N-methylaniline) thin film gradually returned to the original absorbance of the film before addition of ozone to the air. The results show that this poly(N-methylaniline) thin film is useful as an optical sensing material for detection of intermediate to high concentrations of ozone.

Example 11

Figure 6:
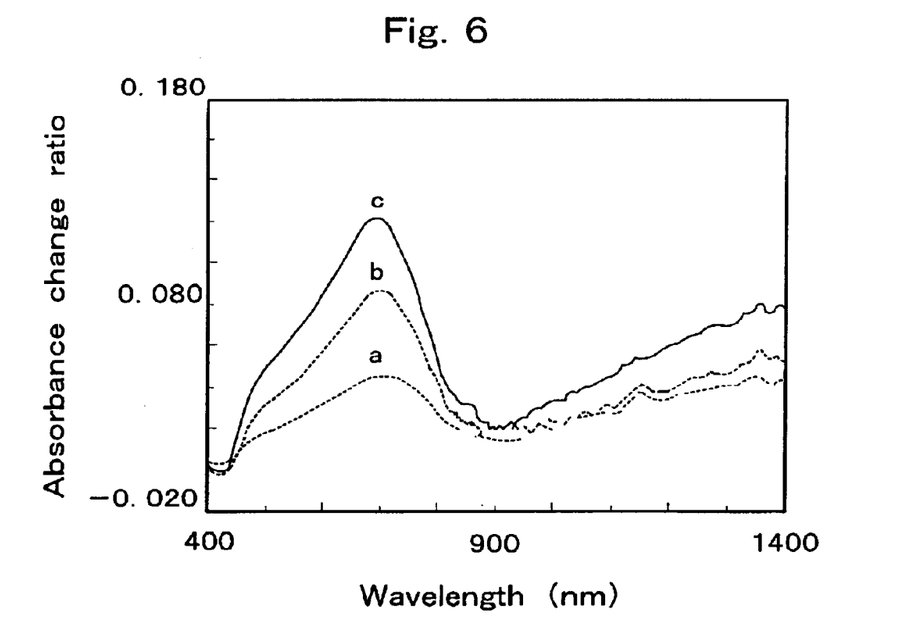
FIG. 6 shows the relationship between the absorbance change ratio of a poly(N-methylaniline) thin film and the wavelength of light in Example 11.

A poly(N-methylaniline) thin film was formed on a polystyrene substrate (the inner walls of a polystyrene cuvette) by chemical oxidation polymerization. The resulting film was oxidized with an oxidant, washed with distilled water and dried, thus giving an ashy green poly(N-methylaniline) thin film (about 600 nm in thickness) in an oxidized and intermediate protonation state. Two poly(N-methylaniline) thin films, with a total thickness of about 1200 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(N-methylaniline) thin film did not change in the presence of 10 ppm or less of ozone but changed in the presence of 25 ppm, 50 ppm or 100 ppm of ozone. Under exposure to 100 ppm of ozone, the change in absorbance of the poly(N-methylaniline) thin film was maximal (largest increase) at a wavelength of around 710 nm. Under exposure to 25 ppm, 50 ppm and 100 ppm of ozone, the absorbance change ratio of the poly(N-methylaniline) thin film was maximal (largest increase) (0.047, 0.089 and 0.124, respectively) at a wavelength of around 710 nm. FIG. 6 shows the relationship between the absorbance change ratio of the poly(N-methylaniline) thin film and the wavelength of light. In FIG. 6, the ozone concentrations are 25 ppm (a), 50 ppm (b) and 100 ppm (c). When the atmosphere was changed from the ozone-containing air to an ozone-free air, the absorbance of the poly(N-methylaniline) thin film gradually returned to the original absorbance of the film before addition of ozone to the air. The results show that this poly(N-methylaniline) thin film is useful as an optical sensing material for detection of intermediate to high concentrations of ozone.

Example 12

A poly(N-methylaniline) thin film was formed on a polystyrene substrate (the inner walls of a polystyrene cuvette) by chemical oxidation polymerization. The resulting film was oxidized with an oxidant, washed with hydrochloric acid and dried, thus giving an ashy greenish-brown poly(N-methylaniline) thin film (about 600 nm in thickness) in an oxidized and protonated state. Two poly(N-methylaniline) thin films, with a total thickness of about 1200 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(N-methylaniline) thin film did not change in the presence of 10 ppm or less of ozone but changed in the presence of 25 ppm, 50 ppm or 100 ppm of ozone. Under exposure to 100 ppm of ozone, the change in absorbance of the poly(N-methylaniline) thin film was maximal (largest increase) at a wavelength of around 750 nm. Under exposure to 25 ppm, 50 ppm and 100 ppm of ozone, the absorbance change ratio of the poly(N-methylaniline) thin film was maximal (largest increase) (0.062, 0.113 and 0.135, respectively) at a wavelength of around 720 nm. When the atmosphere was changed from the ozone-containing air to an ozone-free air, the absorbance of the poly(N-methylaniline) thin film gradually returned to the original absorbance of the film before addition of ozone to the air. The results show that this poly(N-methylaniline) thin film is useful as an optical sensing material for detection of intermediate to high concentrations of ozone.

Example 13

Figure 7:
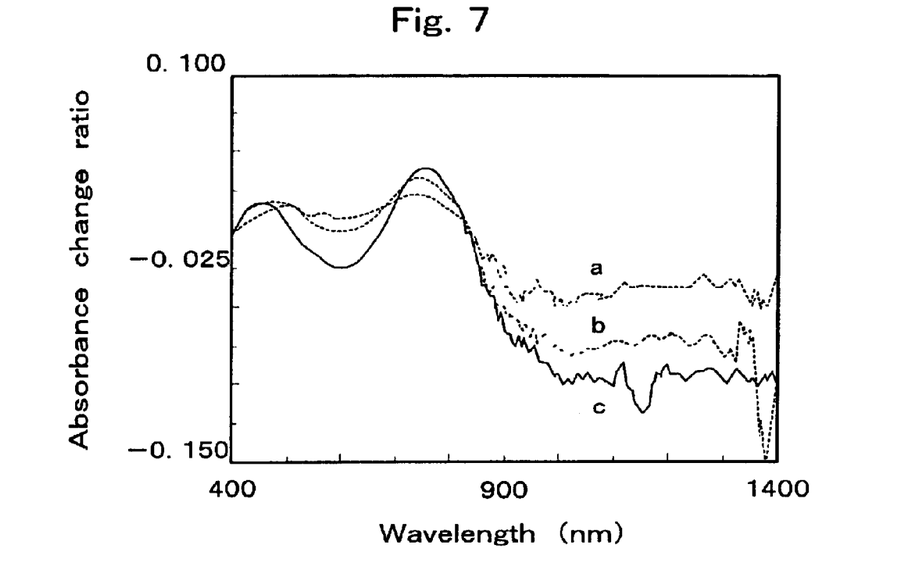
FIG. 7 shows the relationship between the absorbance change ratio of a poly(2-chloroaniline) thin film and the wavelength of light in Example 13.

A poly(2-chloroaniline) thin film was formed on a polystyrene substrate (the inner walls of a polystyrene cuvette) by chemical oxidation polymerization. The resulting film was washed with distilled water and dried, thus giving an ashy blue poly(2-chloroaniline) thin film (about 400 nm in thickness) in an intermediate reduction-oxidation and intermediate protonation state. Two poly(2-chloroaniline) thin films, with a total thickness of about 800 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(2-chloroaniline) thin film did not change in the presence of 10 ppm or less of ozone but changed in the presence of 25 ppm, 50 ppm or 100 ppm of ozone. Under exposure to 100 ppm of ozone, the change in absorbance of the poly(2-chloroaniline) thin film was maximal (largest decrease) at a wavelength of around 930 nm. Under exposure to 25 ppm, 50 ppm and 100 ppm of ozone, the absorbance change ratio of the poly(2-chloroaniline) thin film was maximal (largest decrease) (−0.049, −0.079 and −0.117, respectively) at a wavelength of around 990 nm. FIG. 7 shows the relationship between the absorbance change ratio of the poly(2-chloroaniline) thin film and the wavelength of light. In FIG. 7, the ozone concentrations are 25 ppm (a), 50 ppm (b) and 100 ppm (c). When the atmosphere was changed from the ozone-containing air to an ozone-free air, the absorbance of the poly(2-chloroaniline) thin film gradually returned to the original absorbance of the film before addition of ozone to the air. The results show that this poly(2-chloroaniline) thin film is useful as an optical sensing material for detection of intermediate to high concentrations of ozone. When ozone was added to air with a relative humidity of 20% and to air with a relative humidity of 80%, results similar to the above were obtained. When the poly(2-chloroaniline) thin film was formed on a glass substrate and on a quartz substrate by chemical oxidation polymerization, absorbance changes due to ozone were similar to the above.

Example 14

A poly(2-chloroaniline) thin film was formed on a polystyrene substrate (the inner walls of a polystyrene cuvette) by chemical oxidation polymerization. The resulting film was reduced with a reducing agent, washed with an aqueous sodium hydroxide solution and dried, thus giving an ashy blue poly(2-chloroaniline) thin film (about 400 nm in thickness) in a reduced and deprotonated state. Two poly(2-chloroaniline) thin films, with a total thickness of about 800 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(2-chloroaniline) thin film did not change in the presence of 10 ppm or less of ozone but changed in the presence of 25 ppm, 50 ppm or 100 ppm of ozone. Under exposure to 100 ppm of ozone, the change of absorbance of the poly(2-chloroaniline) thin film was maximal (largest increase) at a wavelength of around 780 nm. Under exposure to 50 ppm and 100 ppm of ozone, the absorbance change ratio of the poly(2-chloroaniline) thin film was maximal (largest increase) (0.026 and 0.036, respectively) at a wavelength of around 790 nm. When the atmosphere was changed from the ozone-containing air to an ozone-free air, the absorbance of the poly(2-chloroaniline) thin film gradually returned to the original absorbance of the film before addition of ozone to the air. The results show that this poly(2-chloroaniline) thin film is useful as an optical sensing material for detection of a relatively high concentration of ozone.

Example 15

Figure 8:
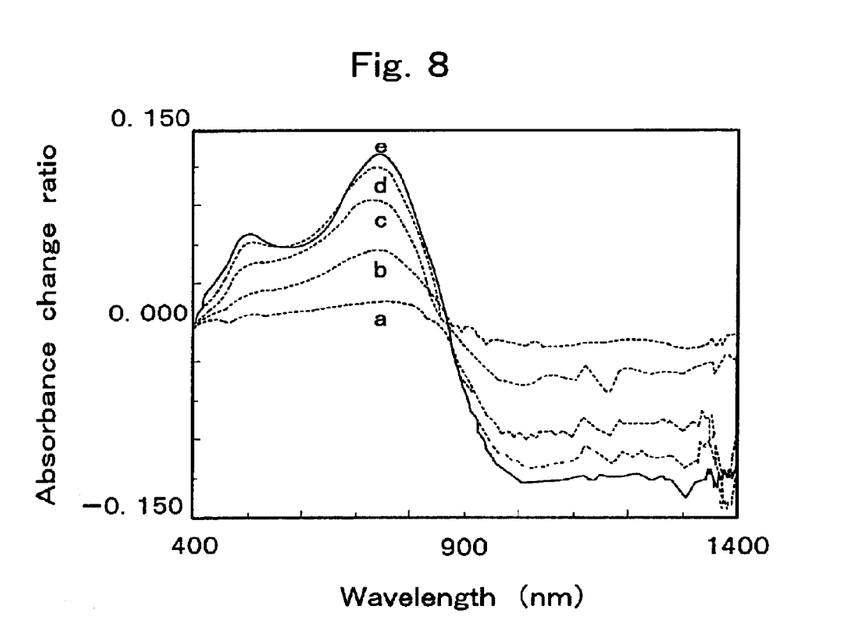
FIG. 8 shows the relationship between the absorbance change ratio of a poly(2-chloroaniline) thin film and the wavelength of light in Example 15.

A poly(2-chloroaniline) thin film was formed on a polystyrene substrate (the inner walls of a polystyrene cuvette) by chemical oxidation polymerization. The resulting film was reduced with a reducing agent, washed with distilled water and dried, thus giving an ashy bluish-green poly(2-chloroaniline) thin film (about 400 nm in thickness) in a reduced and intermediate protonation state. Two poly(2-chloroaniline) thin films, with a total thickness of about 800 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(2-chloroaniline) thin film changed in the presence of ozone in all of the above concentrations. Under exposure to 100 ppm of ozone, the change in absorbance of the poly(2-chloroaniline) thin film was maximal (largest increase) at a wavelength of around 760 nm. Under exposure to 2.5 ppm, 10 ppm, 25 ppm, 50 ppm and 100 ppm of ozone, the absorbance change ratio of the poly(2-chloroaniline) thin film was maximal (largest increase) (0.017, 0.056, 0.096, 0.121 and 0.132, respectively) at a wavelength of around 760 nm. FIG. 8 shows the relationship between the absorbance change ratio of the poly(2-chloroaniline) thin film and the wavelength of light. In FIG. 8, the ozone concentrations are 2.5 ppm (a), 10 ppm (b), 25 ppm (c), 50 ppm (d) and 100 ppm (e). When the atmosphere was changed from the ozone-containing air to an ozone-free air, the absorbance of the poly(2-chloroaniline) thin film gradually returned to the original absorbance of the film before addition of ozone to the air. The results show that this poly(2-chloroaniline) thin film is useful as an optical sensing material for the detection of ozone over a wide range of concentrations. When ozone was added to air with a relative humidity of 20% and to air with a relative humidity of 80%, results similar to the above were obtained. Electrodes were attached to a poly(2-chloroaniline) thin film formed on a glass substrate by chemical oxidation polymerization as above and to poly(2-chloroaniline) pellets formed by compressing the powder. The electrical conductivity change of the poly(2-chloroaniline) thin film when exposed to 100 ppm of ozone was measured. The results show that electrical conductivity of the poly(2-chloroaniline) thin film increases in the presence of ozone and the thin film is useful as an electrical sensing material for ozone detection.

Example 16

A poly(2-chloroaniline) thin film was formed on a polystyrene substrate (the inner walls of a polystyrene cuvette) by chemical oxidation polymerization. The resulting film was reduced with a reducing agent, washed with hydrochloric acid and dried, thus giving an ashy green poly(2-chloroaniline) thin film (about 400 nm in thickness) in a reduced and protonated state. Two poly(2-chloroaniline) thin films, with a total thickness of about 800 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(2-chloroaniline) thin film changed in the presence of ozone in all of the above concentrations. Under exposure to 100 ppm of ozone, the change in absorbance of the poly(2-chloroaniline) thin film was maximal (largest increase) at a wavelength of around 850 nm. Under exposure to 2.5 ppm, 10 ppm, 25 ppm, 50 ppm and 100 ppm of ozone, the absorbance change ratio of the poly(2-chloroaniline) thin film was maximal (largest increase) (0.013, 0.045, 0.157, 0.234 and 0.297, respectively) at a wavelength of around 850 nm. When the atmosphere was changed from the ozone-containing air to an ozone-free air, the absorbance of the poly(2-chloroaniline) thin film gradually returned to the original absorbance of the film before addition of ozone to the air. The results show that this poly(2-chloroaniline) thin film is useful as an optical sensing material for the detection of ozone over a wide range of concentrations. When ozone was added to air with a relative humidity of 20% and to air with a relative humidity of 80%, results similar to the above were obtained.

Example 17

A poly(2-chloroaniline) thin film was formed on a polystyrene substrate (the inner walls of a polystyrene cuvette) by chemical oxidation polymerization. The resulting film was oxidized with an oxidant, washed with an aqueous sodium hydroxide solution and dried, thus giving a purple poly(2-chloroaniline) thin film (about 400 nm in thickness) in an oxidized and deprotonated state. Two poly(2-chloroaniline) thin films, with a total thickness of about 800 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(2-chloroaniline) thin film did not change in the presence of 2.5 ppm or less of ozone but changed in the presence of 10 ppm, 25 ppm, 50 ppm or 100 ppm of ozone. Under exposure to 100 ppm of ozone, the change in absorbance of the poly(2-chloroaniline) thin film was maximal (largest decrease) at a wavelength of around 580 nm. Under exposure to 10 ppm, 25 ppm, 50 ppm and 100 ppm of ozone, the absorbance change ratio of the poly(2-chloroaniline) thin film was maximal (largest decrease) (−0.008, −0.032, −0.064 and −0.089, respectively) at a wavelength of around 630 nm. When the atmosphere was changed from the ozone-containing air to an ozone-free air, the absorbance of the poly(2-chloroaniline) thin film gradually returned to the original absorbance of the film before addition of ozone to the air. The results show that this poly(2-chloroaniline) thin film is useful as an optical sensing material for detection of intermediate to high concentrations of ozone.

Example 18

A poly(2-chloroaniline) thin film was formed on a polystyrene substrate (the inner walls of a polystyrene cuvette) by chemical oxidation polymerization. The resulting film was oxidized with an oxidant, washed with distilled water and dried, thus giving an ashy blue poly(2-chloroaniline) thin film (about 400 nm in thickness) in an oxidized and intermediate protonation state. Two poly(2-chloroaniline) thin films, with a total thickness of about 800 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(2-chloroaniline) thin film did not change in the presence of 10 ppm or less of ozone but changed in the presence of 25 ppm, 50 ppm or 100 ppm of ozone. Under exposure to 100 ppm of ozone, the change in absorbance of the poly(2-chloroaniline) thin film was maximal (largest decrease) at a wavelength of around 900 nm. Under exposure to 25 ppm, 50 ppm and 100 ppm of ozone, the absorbance change ratio of the poly(2-chloroaniline) thin film was maximal (largest decrease) (−0.077, −0.089 and −0.144, respectively) at a wavelength of around 1170 nm. When the atmosphere was changed from the ozone-containing air to an ozone-free air, the absorbance of the poly(2-chloroaniline) thin film gradually returned to the original absorbance of the film before addition of ozone to the air. The results show that this poly(2-chloroaniline) thin film is useful as an optical sensing material for detection of intermediate to high concentrations of ozone. When ozone was added to air with a relative humidity of 20% and to air with a relative humidity of 80%, results similar to the above were obtained.

Example 19

Figure 9:
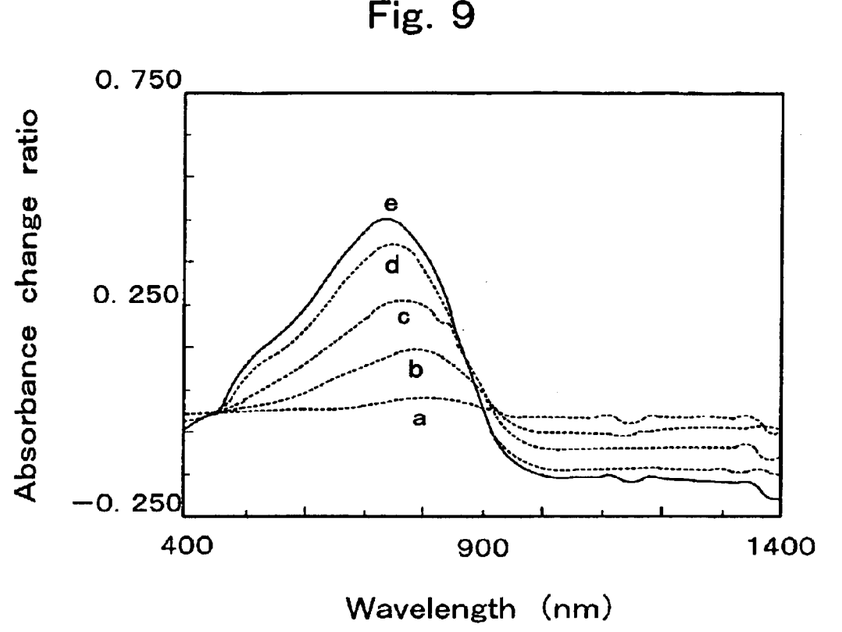
FIG. 9 shows the relationship between the absorbance change ratio of a poly(2-chloroaniline) thin film and the wavelength of light in Example 19.

A poly(2-chloroaniline) thin film was formed on a polystyrene substrate (the inner walls of a polystyrene cuvette) by chemical oxidation polymerization. The resulting film was oxidized with an oxidant, washed with hydrochloric acid and dried, thus giving an ashy bluish-green poly(2-chloroaniline) thin film (about 400 nm in thickness) in an oxidized and protonated state. Two poly(2-chloroaniline) thin films, with a total thickness of about 800 nm, were exposed to air with a relative humidity of 50% and then subjected to air to which 2.5 ppm, 10 ppm, 25 ppm, 50 ppm or 100 ppm of ozone was added. The visible to near-IR absorbance of the poly(2-chloroaniline) thin film changed in the presence of ozone in all of the above concentrations. Under exposure to 100 ppm of ozone, the change in absorbance of the poly(2-chloroaniline) thin film was maximal (largest increase) at a wavelength of around 840 nm. Under exposure to 2.5 ppm, 10 ppm, 25 ppm, 50 ppm and 100 ppm of ozone, the absorbance change ratio of the poly(2-chloroaniline) thin film was maximal (largest increase) (0.040, 0.148, 0.264, 0.395 and 0.459, respectively) at a wavelength of around 840 nm. FIG. 9 shows the relationship between the absorbance change ratio of the poly(2-chloroaniline) thin film and the wavelength of light. In FIG. 9, the ozone concentrations are 2.5 ppm (a), 10 ppm (b), 25 ppm (c), 50 ppm (d) and 100 ppm (e). When the atmosphere was changed from the ozone-containing air to an ozone-free air, the absorbance of the poly(2-chloroaniline) thin film gradually returned to the original absorbance of the film before addition of ozone to the air. The results show that this poly(2-chloroaniline) thin film is useful as an optical sensing material for the detection of ozone over a wide range of concentrations. When ozone was added to air with a relative humidity of 20% and to air with a relative humidity of 80%, results similar to the above were obtained.

Example 20

A polyaniline thin film was formed on a substrate having a gold electrode by electrolytic oxidation polymerization. The resulting film was washed with distilled water and dried, thus giving a pale blue polyaniline thin film (about 300 nm in thickness) in an intermediate reduction-oxidation and intermediate protonation state. This polyaniline thin film was exposed to air and then subjected to air to which 100 ppm of ozone was added. As a result, the visible to near-IR absorbance of the polyaniline thin film changed and the polyaniline thin film turned dark green. Simultaneously, the electrical conductivity of the polyaniline thin film increased about 20-fold. When the atmosphere was changed from the ozone-containing air to an ozone-free air, the absorbance and electrical conductivity of the polyaniline thin film gradually returned to the original absorbance and electrical conductivity of the film before addition of ozone to the air. The results show that this polyaniline thin film is useful as an optical and/or electrical sensing material for ozone detection.

What is claimed:

1. An ozone detecting material comprising a polymer prepared by polymerization of at least one monomer selected from the group consisting of aniline having a halogen substituent at the 2-position, aniline having a halogen substituent at the 3-position, aniline having a halogen substituent at the 4-position, aniline having a $C_{1-3}$ alkyl substituent at the N-position, and diphenylamine;

the ozone detecting material being formed into a thin film on a transparent substrate, a waveguide, an optical fiber;

the light absorption rate of the ozone detecting material changing upon contact with an ozone-containing gas.

2. An ozone detecting material comprising:

a polymer prepared by polymerization of at least one monomer selected from the group consisting of aniline having a halogen substituent at the 2-position, aniline having a halogen substituent at the 3-position, aniline having a halogen substituent at the 4-position, aniline having a $C_{1-3}$ alkyl substituent at the N-position, and diphenylamine; and at least one additive component selected from the group consisting of an electro-conductive fine carbon powder, a semiconductive metal oxide and a semiconductive polymer material, the ratio of the number of monomer units in the polymer of claim 1 to the sum of the number of carbon atoms in the electro-conductive fine carbon powder, the number of atoms other than oxygen in the semiconductive metal oxide and the number of monomer units constituting the semiconductive polymer material being in the range of 1:0.01 to 1:1;

wherein an electro-conductive fine carbon powder is present as an additive component.

3. An ozone detecting material comprising:

a polymer prepared by polymerization of at least one monomer selected from the group consisting of aniline having a halogen substituent at the 2-position, aniline having a halogen substituent at the 3-position, aniline having a halogen substituent at the 4-position, aniline having a $C_{1-3}$ alkyl substituent at the N-position, and diphenylamine; and at least one additive component selected from the group consisting of an electro-conductive fine carbon powder, a semiconductive metal oxide and a semiconductive polymer material, the ratio of the number of monomer units in the polymer of claim 1 to the sum of the number of carbon atoms in the electro-conductive fine carbon powder, the number of atoms other than oxygen in the semiconductive metal oxide and the number of monomer units constituting the semiconductive polymer material being in the range of 1:0.01 to 1:1;

wherein a semiconductive metal oxide selected from the group consisting of tin oxide, indium oxide, titanium oxide, vanadium oxide, manganese oxide, iron oxide, nickel oxide, copper oxide and tungsten oxide, is present as an additive component.

* * * * *